(12) United States Patent
Heinonen

(10) Patent No.: US 8,033,280 B2
(45) Date of Patent: Oct. 11, 2011

(54) INHALATION ANAESTHESIA DELIVERY SYSTEM AND A METHOD FOR LEAK DETECTION IN THE INHALATION ANAESTHESIA DELIVERY SYSTEM

(75) Inventor: Erkki Paavo Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 904 days.

(21) Appl. No.: 12/034,198

(22) Filed: Feb. 20, 2008

(65) Prior Publication Data

US 2008/0202526 A1 Aug. 28, 2008

(30) Foreign Application Priority Data

Feb. 23, 2007 (EP) ..................................... 07102940

(51) Int. Cl.
*A61M 11/00* (2006.01)
(52) U.S. Cl. ......... 128/204.22; 128/203.13; 128/203.12; 128/204.21

(58) Field of Classification Search ............. 128/204.21, 128/204.22, 203.13, 203.12, 205.28, 205.27, 128/200.24, 205.12, 205.29
See application file for complete search history.

(56) References Cited

U.S. PATENT DOCUMENTS

| 5,831,147 | A * | 11/1998 | Hoath | 73/49.3 |
|---|---|---|---|---|
| 6,319,375 | B1 * | 11/2001 | Warburton | 204/409 |
| 7,832,398 | B2 * | 11/2010 | Laurila | 128/203.13 |
| 2008/0223109 | A1 * | 9/2008 | Nitta et al. | 73/23.2 |
| 2008/0236583 | A1 * | 10/2008 | Tigerstedt | 128/204.22 |

* cited by examiner

*Primary Examiner* — Steven Douglas
(74) *Attorney, Agent, or Firm* — Global Patent Operation; Jonathan E. Thomas

(57) ABSTRACT

Inhalation anaesthesia delivery system and a leak detecting method, whereby the system comprises a fresh gas feeding arrangement connected to a breathing circuit, a monitor device, The monitor device is configured to monitor gas concentrations in the breathing circuit by using a sampling line. The monitor device is configured to measure at least two gas components' concentrations and identify changes, which are simultaneous towards the known ambient air concentration values of the two gas components' concentrations measured.

13 Claims, 2 Drawing Sheets

Figure 1:
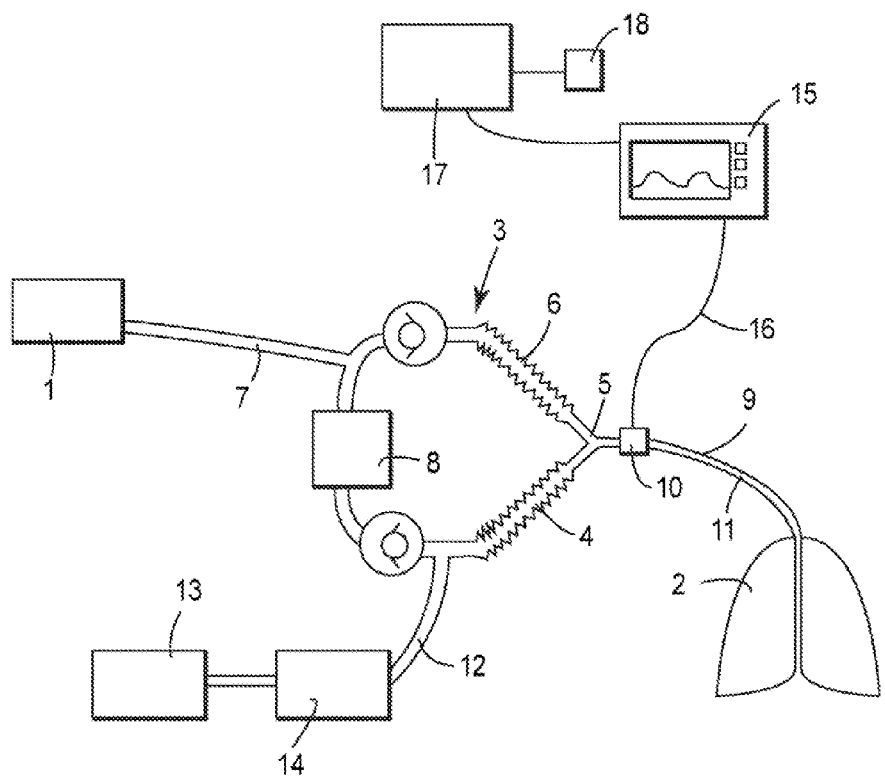

INHALATION ANAESTHESIA DELIVERY SYSTEM AND A METHOD FOR LEAK DETECTION IN THE INHALATION ANAESTHESIA DELIVERY SYSTEM

The invention relates to an inhalation anaesthesia delivery system comprising a fresh gas feeding arrangement connected to a breathing circuit and a monitor device, whereby the monitor device is configured to monitor gas concentrations in the breathing circuit by using a sampling line. The invention relates also to a method for detection of leak while measuring patient breathing gas.

Inhalation anaesthesia delivery systems are used to maintain oxygen (O2) and carbon dioxide (CO2) exchange of the patient during anaesthesia when patient breathing is disabled due to muscular relaxation. For this purpose, ventilator is pressurizing patient lungs to deliver fresh gas during inspiration. Lung elasticity forces the gas out from the lungs when the ventilator allows the pressure release during expiration. Inspiration and expiration together form a breath. The amount of delivered gas in single breath is called tidal volume.

Breathing gas is often mixed with anaesthesia gases to provide inhalation anaesthesia. These gases are nitrous oxide (N2O) that is used as an alternate gas instead of air, and volatile anaesthetics that are vaporized into the breathing gas. Patient concentration of the N2O seldom exceeds range 30%-75% whereas the volatile agent concentrations vary depending on die agent from 0.7% (halothane) to 3% (sevoflurane, enflurane, isoflurane) and even further up to 6%-12% with desflurane. Patient concentration determines gas exchange status (O2, CO2) and the depth of anaesthesia of the patient. It is measured as end-expiration (end-tidal) breathing gas concentration. In addition to this, also inspiration gas concentrations are sometimes measured.

The measured end-tidal (Et) concentration is used as dominant input parameter to control the breathing volume and breathing gas mixture. Therefore the accuracy of the measured value acts primary importance regarding the safety of the control. Based on this information, the operator adjusts the ventilation to maintain expected end-tidal CO2 concentration and fresh gas flow aid mixture concentrations for O2 and volatile agents to maintain the patient concentrations of these gases.

Breathing gas mixture is measured with gas analyzers. Most of these have a sampling system to draw the sampling gas from the sampling site into the gas concentration sensitive detector measuring the concentration. Such devices are called side-stream analyzers. Within the analyzer the CO2. N2O, and volatile agents are commonly measured using infrared absorption spectrometers whereas O2 sensor is based on the paramagnetic characteristics of the gas.

Patient breathing gas control is traditionally performed manually by an anaesthesia, operator. Recent development, however ask for increase in safety and efficacy, which promotes automatic control loops controlling the breathing actuators in response to the measured patient values. Increased automation free up the human resources in operating room to concentrate on patient instead of the machine, or even take care of more patients at the same time. This further emphasizes the measured data accuracy requirement.

Traditionally in closed loop control systems the gas monitor accuracy has been verified by duplicating the gas measurement. Would the results differ from each other, the feedback control system is then cut off and the error situation alarmed. An example of such system is enclosed in US 2005/0103338. This is however expensive solution that also increases the workload of the operator in setting up the system. This also increases gas consumption when two monitors are suctioning the sampling gas, unless the gas flows are not returned to the circuit, which creates problem of sensor contamination. EP 1140264 provides an alternate solution to validate the monitor measurement with periodical sampling of the fresh gas mixture, tire concentrations of which are known. The solution described in EP 1140264, however needs improvement to detect sampling gas line leak. When sampling the fresh gas line, the sampling gas line is by passed and the possible leak there remains unobserved. Sampling line leak allows ambient gas to be drawn into the sampling system diluting the breathing gas. As a result of this, the measured concentrations will approach the ambient value that is zero for CO2, N2O, and volatile agents, and 21% for O2. Would a leak occur, the erroneously low patient gas values are then compensated, either by the operator manually, or by the automated controller, with reduced ventilation, increased delivery of O2, and increased delivery of volatile agents. At the worst, this ends up to compromised CO2 removal and agent overdose. If undetected, the latter may end up to patient health hazard.

The object of the invention is to obtain a system to detect sampling gas line leak occurring during patient monitoring. Clinical situations where such leak may occur are loose connection of the sampling line to gas monitor, faulty sampling line, or removed water trap often present in gas sampling system for water separation. This is obtained with the invention. The system of the invention is characterized in that the monitor device is configured to measure at least two gas components' concentrations and identity changes which are simultaneous towards the known ambient air concentration values of the two gas components' concentrations measured, which identifies leak in the sampling line. The method of the invention is characterized in that at least two gas components' concentrations are measured and changes, which are simultaneous towards the known ambient air concentration values of the two gas components' concentrations measured are identified, which identifies leak in the sampling line.

As described above the invention is based on identification of simultaneous changes in at least two measured gas concentrations. Such gases are for example CO2 and O2. When leak occurs, the measured concentrations encounter simultaneously a change equal in magnitude towards the ambient values, which are 0.03% for CO2 and 20.9% for O2.

Recover from the leak (sealing) can be respectively identified with simultaneous increase of the values. Advantageously the algorithm may search for changes in EtCO2 and EtO2 values. When EtO2 value is close to the ambient value, FiO2 can be used instead. Also N2O or volatile agent concentration could be used, but the disadvantage of those for a general algorithm is that those are not continuously present in the breathing circuit. Also concentration curve forms can be used to search the changes instead of the Et and Fi values.

The signals used on the leak detection experience changes up and down as a response of various clinical actions during ventilation. However, no single action except sampling line leak causes both O2 and CO2 to approach towards ambient gas concentration simultaneously. This can happen only when two separate items occur simultaneously. To reduce the risk for fault alarms, the algorithm of the invention further validates the magnitude of change towards the ambient value, in assessment of the signals, fuzzy logic principle capable of drawing conclusions even from imprecise information provides ideal approach for this multi-parameter analysis.

As described above the invention is intended for detecting a sampling line leak occurring during patient monitoring, and therefore a separate initial check procedure must be carried out to make clear that tire system is originally tight. Said initial check procedure can be carried out in any appropriate way.

This invention allows improved safety of anaesthesia delivery by alarming a safety endangering condition. This has special value in feedback control systems where anaesthesia vaporization is controlled automatically for set anaesthetic concentration in patient lungs as well as ventilation control with EtCO2.

The advantage of the invention in detecting the sampling line leak is also in that it applies the gases and equipment normally present in the breathing circuit.

Figure 2:
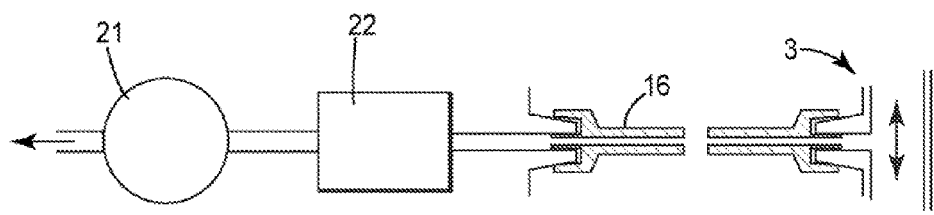
Figure 3:
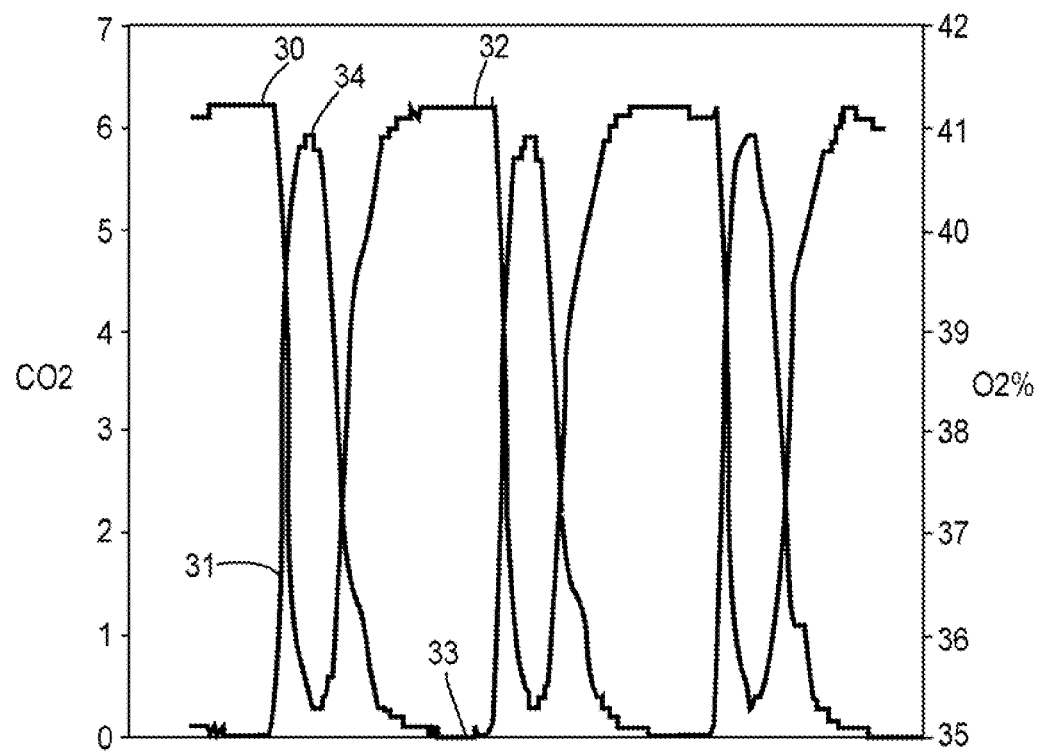
Figure 4:
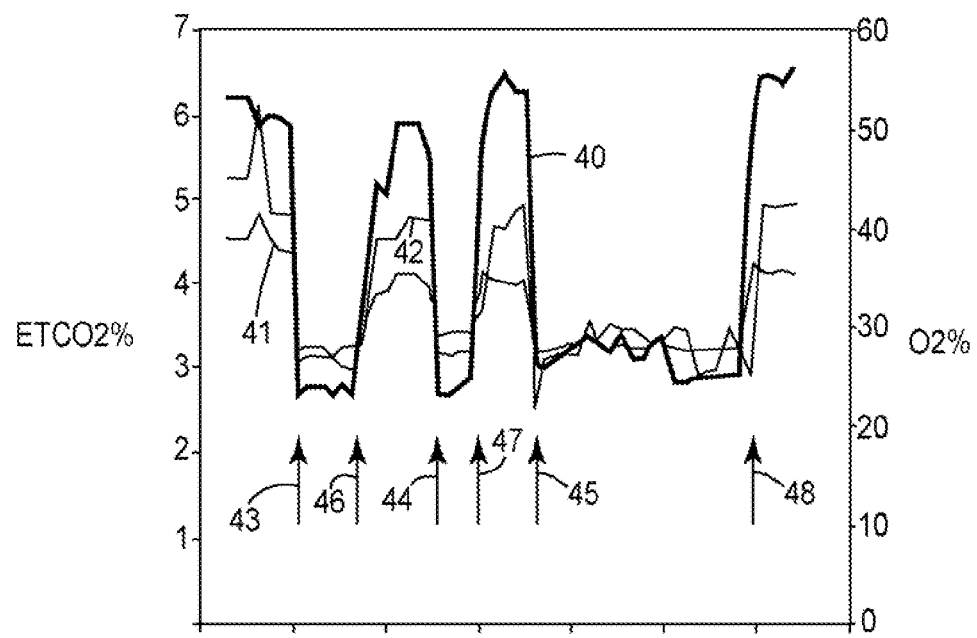

In the following the invention will be described in greater detail by means of examples shown in the attached drawing, in which FIG. 1 shows schematically an operational environment of the system according to the invention, FIG. 2 shows a simplified gas monitor sampling system, FIG. 3 shows CO2 and O2 concentration waveforms in patient breathing, and FIG. 4 shows an example of synchronized breath values EtCO2, EtO2 and FiO2.

FIG. 1 shows the anaesthesia environment the invention may be applied. Ventilator 1 fills patient lungs 2 during inspiration by pressurizing the breathing circuit 3. Breathing circuit comprises of inspiration limb 4, Y-piece 5, expiration limb 6, ventilator limb 7, CO2 absorber 8, and patient limb 9. Inspiration and expiration limbs include unidirectional valve to direct the inspiration and expiration gas flow to respective limbs. Patient limb includes gas monitor sampling port 10 and intubation tube 11 connecting the patient with the breathing circuit.

Alternatively patient may be breathing spontaneously. In spontaneous breathing the ventilator comprises reservoir collecting the exhalation gas and therefrom patient breathing action receives inspiration gas.

In operation, ventilator receives the expired gas from the patient during expiration and stores the gas for the next inspiration. At inspiration the gas is guided through CO2 absorber where the CO2 is removed to inspiration limb and further to patient lungs. Breathing gas is brought into the breathing circuit from fresh gas line 12. The fresh gas is a mixture of O2, N2O, N2 (air) or xenon from gas regulating unit 13 and volatile agents vaporized into this gas stream in the vaporizer 14.

Monitor means 15, i.e. gas monitor includes a pump generating vacuum pressure and suctioning the breathing gas through sampling line 16 for analysis in the side-stream gas sensors within the monitor. The sampling line is a capillary tube with typical bore diameter 0.8-1.4 mm and length 2-4 m. Sampling gas flow varies from 50 to 200 mL/min.

Monitor means 15 may still be further electrically connected to control device 17, which may be further connected to the actuators (ventilator, gas regulating unit, and/or vaporizer) to close the control loop. This controller compares the measured values with the user given target and tunes the actuators to match the measured values with the setting. The target value, i.e. the desired concentration is set by using an interface unit 18.

FIG. 2 shows a simplified gas monitor sampling system. Breathing circuit 3 pressure varies typically from 10 to 50 cmH2O inspiration peak overpressure to 3-15 cmH2O expiration overpressure. Breathing gas sample pump 21 generates vacuum e.g. 100 cmH2O below environment. The pressure difference is spread between the gas sensors 22, sampling line 16, and some other components like zeroing valve (not shown). As a result of this, the pressure within the monitor end of the sampling line 16 stays typically below ambient. Thus, would this contact get loose, ambient gas enters the sampling gas stream diluting the breathing gas before analysis in gas sensors ending up to analysis error. Diluting leak may occur at any joint where the prevailing pressure is below ambient. In this connection it must be understood that when discussing a leak in connection with die sampling line the term sampling line must be understood widely, i.e. said term include here also sampling port 10, eventual connector elements etc. An example of such is sampling line water separation system equipped with detachable liquid accumulation cup.

When leak occur, all breathing gas concentrations dilute towards the ambient concentration at the same time. When leak occur the changes in concentrations are also essentially equal in magnitude of change. It must be noted that when we say here essentially equal in magnitude we mean that the changes are essentially of the same order of magnitude. Analysis of changes for more than one gas reveals the leak. Advantageously this analysis is performed for CO2 and O2, because those are always present in patient breathing.

FIG. 3 presents CO2 concentration waveform 30 and O2 concentration waveform 31 with reference to time on abscissa. As shown, normal breathing pattern, includes up-going changes as well as down-going changes. Therefore the leak detection changes are advantageously synchronized with breath pattern. End-tidal values 32 and 33 provide such synchronized value that are different to ambient air values in normal anaesthesia settings. Sometimes the EtO2 value can be close to the ambient air value, in these circumstances inspired O2(FiO2) concentration 34 can be used instead.

FIG. 4 shows an example of synchronized breath values EtCO2 40, EtO2 41, and FiO2 42 in experimental setting where leak occurs at 43, 44, and 45 and respectively becomes sealed at 46, 47, and 48. The graph shows EtCO2 to be diluted from the level of 6% to the level of 3% because of sampling line leak. Respectively EtO2 decreases from 35% to 28% and FiO2 from 42% to 30%.

When leak occurs, the breathing gas becomes diluted with the ambient gas. The concentration after this dilution can be calculated from the equation $$F\%\,(m) = (\text{leak}\%*F\%\,(\text{amb}) + (100 - \text{leak}\%)*F\%\,(\text{bg}))/100 \tag{1}$$

Where

F % (m)=Measured gas concentration of the particular gas

Leak %=proportion of the leak from the total sampling gas flow

F % (amb)=Ambient gas concentration of the particular gas

F % (bg)=Breathing gas concentration of the particular gas

When leak occurs, measured gas concentration changes from the previous value equal to F % (bg) to F % (m). This change is then related with the change potential that is F % (bg)–F % (arob) giving the value for the rate of change $$(F\%\,(m) - F\%\,(\text{bg}))/(F\%\,(\text{bg}) - F\%\,(\text{amb})) \tag{2}$$

Negative result indicates leak to occur whereas positive result indicates sealing. This relative change is calculated for at least two gases. When both indicate leak or sealing at the same time, and the magnitude of changes are equal as well, leak or sealing event is identified.

The result of equation (2) are seldom zero, thus they indicate leak or sealing from individual gas. Parallel change may also occur e.g. due to measurement noise or normal physiological variation. Small leak has only minor effect on the measurement; thus those need not to be identified. Larger changes in individual gas may occur due to changes in settings, like fresh gas flows or ventilation. In case of two simultaneous changes in settings both of the gases may change simultaneously. To still enhance the specificity of the method to identify only leak and sealing, identification may take advantage of the fact that dilution is equal to both gases. Identification algorithm may be composed from these rules e.g. by using the principles of fuzzy logic.

As described before the system of the invention detects the occurring leak, not the initial one. Therefore, the initial status has to be confirmed separately. The initial tightness status can be confirmed by using any appropriate procedure.

The embodiment of the invention described above is by no means intended to restrict the invention but the invention can be varied completely freely within the scope of the claims. Therefore it is obvious that the system or its details do not necessary; have to be exactly the same as shown in the figures but other solutions are possible, too. The invention is described above by referring to an embodiment using closed loop principle. It must however be understood that the invention is also fully usable in connection with a manually operated frosh gas control system.

The invention claimed is:

1. An inhalation anaesthesia delivery system, comprising: a fresh gas feeding arrangement connected to a breathing circuit and a monitor device, wherein the monitor device is configured to monitor gas concentrations in the breathing circuit by using a sampling line, and wherein the monitor device is configured to measure at least two gas components' concentrations and identify changes, which are simultaneous towards the known ambient air concentration values of the two gas components' concentrations measured, which identifies leak in the sampling line.

2. The inhalation anaesthesia delivery system of claim 1, wherein the monitor device is configured to measure and identify the changes which are essentially equal in magnitude.

3. The inhalation anaesthesia delivery system of claim 1, wherein the monitor device is configured to identify changes in CO2 and O2 concentrations.

4. The inhalation anaesthesia delivery system of claim 3, wherein the monitor device is configured to identify changes in end tidal CO2 (EtCO2) and end tidal O2 (EtO2) values.

5. The inhalation anaesthesia delivery system of claim 3, wherein the monitor device is configured to identify changes in inspired O2 (FiO2) concentration values.

6. The inhalation anaesthesia delivery system of claim 3, wherein the monitor device is configured to identify the changes by using concentration curve forms.

7. The inhalation anaesthesia delivery system of claim 1, wherein the system further comprises a ventilator.

8. A method for detecting a leak while measuring patient breathing gas in an anaesthesia delivery system, the method comprising:
monitoring gas concentrations in a breathing circuit by using a sampling line,
measuring at least two gas components' concentrations; and
identifying changes, which are simultaneous towards the known ambient air concentration values of the two gas components' concentrations, to identify a leak in the sampling line.

9. The method of claim 8, wherein the changes which are essentially equal in magnitude.

10. The method of claim 8, wherein the at least two gas components are CO2 and O2.

11. The method of claim 10, wherein the identifying changes further comprises identifying changes in end tidal CO2 (EtCO2) and end tidal O2 (EtO2) values.

12. The method of claim 10, wherein the identifying changes further comprises identifying changes in inspired O2 (FiO2) concentration values.

13. The method of claim 10, wherein the identifying changes further comprises using concentration curve forms.

* * * * *